United States Patent
Brodaczewski et al.

(10) Patent No.: US 10,265,079 B2
(45) Date of Patent: Apr. 23, 2019

(54) POLYMERIC LIGATING CLIP

(71) Applicants: Wieslaw Mieczyslaw Brodaczewski, Dubai (AE); Andrzej Janusz Decewicz, Nottingham (GB)

(72) Inventors: Wieslaw Mieczyslaw Brodaczewski, Dubai (AE); Andrzej Janusz Decewicz, Nottingham (GB)

(73) Assignee: GRENA USA LLC, Wilmington, DE (US)

( * ) Notice: Subject to any disclaimer, the term of this patent is extended or adjusted under 35 U.S.C. 154(b) by 48 days.

(21) Appl. No.: 15/466,773

(22) Filed: Mar. 22, 2017

(65) Prior Publication Data

US 2017/0311954 A1 Nov. 2, 2017

Related U.S. Application Data

(60) Provisional application No. 62/328,652, filed on Apr. 28, 2016.

(51) Int. Cl.
*A61B 17/122* (2006.01)
*A61B 17/00* (2006.01)

(52) U.S. Cl.
CPC ... *A61B 17/122* (2013.01); *A61B 2017/00911* (2013.01)

(58) Field of Classification Search
CPC ..... A61B 17/122; A61B 17/12; A61B 17/127; A61B 2017/00911; A61B 17/128
See application file for complete search history.

(56) References Cited

U.S. PATENT DOCUMENTS

| | | |
|---|---|---|
| 4,834,096 A | 5/1989 | Oh et al. |
| 5,062,846 A | 11/1991 | Oh et al. |
| 5,100,416 A | 3/1992 | Oh et al. |
| 6,863,675 B2 | 3/2005 | Wilson, Jr. |
| 6,880,699 B2 | 4/2005 | Gallagher |
| 7,001,412 B2 | 2/2006 | Gallagher et al. |
| 7,211,092 B2 | 5/2007 | Hughett |
| 7,326,223 B2 | 2/2008 | Wilson, Jr. |
| 9,445,820 B2 | 9/2016 | Whiting |

(Continued)

FOREIGN PATENT DOCUMENTS

| | | |
|---|---|---|
| EM | 00079772 | 1/2009 |
| WO | 2013040467 A2 | 3/2013 |

OTHER PUBLICATIONS

International Search Report, dated Aug. 24, 2017.

*Primary Examiner* — Todd J Scherbel
*Assistant Examiner* — Brooke Labranche
(74) *Attorney, Agent, or Firm* — Seth Natter; Natter & Natter (57) ABSTRACT

A one piece molded polymeric ligating clip comprises a pair of curved legs having a unitary hinge at a proximal end and a latch at a distal end. The inner face of each leg includes two rows of transverse ribs, with the rows separated from one another along a longitudinal center line of each leg. The ribs of one row are staggered with respect to the ribs of the other row of the same leg as well as ribs of the corresponding rows on the other leg. Each rib includes a sloped flexible tapered sharp pointed prong which projects away from the inner face of the respective leg and toward the longitudinal center of the leg. The sharp pointed prongs impale the vessel wall when the clip is closed around a vessel or duct.

20 Claims, 10 Drawing Sheets

(56) References Cited

U.S. PATENT DOCUMENTS

| | | | |
|---|---|---|---|
| 9,456,824 B2 * | 10/2016 | Willett | A61B 17/128 |
| 2005/0165423 A1 | 7/2005 | Gallagher et al. | |
| 2006/0217749 A1 | 9/2006 | Wilson | |
| 2009/0088783 A1 | 4/2009 | Kennedy | |
| 2009/0171380 A1 | 7/2009 | Whiting | |

* cited by examiner

POLYMERIC LIGATING CLIP

RELATED APPLICATIONS

This application claims the benefit of Provisional Application No. 62/328,652 filed Apr. 28, 2016, the entirety of which is incorporated herein by reference.

BACKGROUND OF THE INVENTION

1. Field of the Invention

This invention relates generally to surgical clips and more particularly to polymeric ligating clips having improved retention 2. Antecedents of the Invention Numerous surgical procedures require cutting blood vessels and ducts which might require temporary or permanent ligation. Ligation of vessels or other tissues can be performed by closing the vessel with a ligating clip, or by suturing the vessel with surgical thread. Ligation by suturing required complex and difficult time-consuming manipulations of a needle and suture material. Such complex manipulations were often difficult to perform and diverted attention to the surgical procedure itself. Accordingly, the employment of ligating clips, which are relatively easy and quick to apply has grown dramatically.

Hemostatic and aneurysm clips have been used in surgery for ligating blood vessels or other tissues to stop the flow of blood. Such clips have also been used for interrupting or occluding ducts and vessels in particular surgeries. Ligating clips have been applied to the vessel or other tissue by using a surgical clip applies, ligating clip applies, or hemostatic clip applier.

While metallic ligating clips have been employed, metallic clips have been found to interfere with the imaging techniques such as computer tomography and magnetic resonance imaging. To overcome such limitations, biocompatible polymers have been increasingly used for ligating clips. Unlike metallic clips, which are usually symmetric, polymeric clips are usually asymmetric.

These polymeric ligating clips generally comprise a pair of curved legs joined at their proximal ends with an integral hinge. The distal end of one leg terminates in a hook into which the distal end of the other leg securely fits to lock the legs together. The distal ends of the legs of the clips disclosed in U.S. Pat. No. 4,834,096 include lateral bosses that are engaged by jaws of a clip applier which is employed to close the clip around the tissue to be ligated, and to latch or lock the clip in the closed condition. In operation, the jaws of the clip applier are actuated to force the bosses toward one another. This causes the legs to pivot inwardly about the hinge, thereby deflecting the hook of the one leg to allow reception therein of the distal end of the other leg.

Ligating clips must have a sufficient degree of clamping force and retention on a vessel or duct, so as not to move relative to the vessel or duct when applied, while also preserving tissue integrity and minimizing tissue damage. Among the previous approaches at attaining the appropriate retention were spaced ribs extending transversely across the inner face of each leg as disclosed in U.S. Pat. No. 5,062,846, a collapsible flexible rib extending longitudinally along the inner face of a leg, as disclosed in U.S. Pat. No. 9,445,820 and a rib extending longitudinally along the inner face of a leg which seats in a groove formed in the inner face of the other leg, as disclosed in Publication No. 2005/0165423 A1.

There remained a need however; to provide a ligating clip capable of being firmly secured to the tissue or vessel walls without slippage with a minimum level of damage to tissue or vessel walls.

SUMMARY OF THE INVENTION

A one piece molded polymeric ligating clip comprises a pair of curved legs having a unitary hinge at a proximal end and a latch at a distal end. The inner face of each leg includes two rows of transverse ribs, with the rows separated from one another along a longitudinal center line of each leg.

The ribs of one row are staggered with respect to the ribs of the other row of the same leg as well as ribs of the corresponding row on the other leg. Each rib includes a sharp prong which projects away from the inner face of the leg and toward the longitudinal center line of the leg. As the legs close around a vessel or tissue, the prongs impale the vessel wall or tissue for improved retention and eliminate slippage.

From the foregoing compendium, it will be appreciated that an aspect of the present invention is to provide a polymeric ligating clip of the general character described which is not subject to the aforementioned disadvantages of the antecedents of the invention.

A feature of the present invention is to provide a polymeric ligating clip of the general character described which securely ligates vascular walls with minimal tissue trauma.

A consideration of the present invention is to provide a polymeric ligating clip of the general character described which securely ligates vascular walls while precluding slippage between the vascular walls and the clip.

Another aspect of the present invention is to provide a polymeric ligating clip of the general character described which is well suited for employment with conventional applicators.

A further feature of the present invention is to provide a polymeric ligating clip of the general character described which is well suited for economical mass production fabrication.

An additional consideration of the present invention is to provide a polymeric ligating clip of the general character described which is relatively simple to use.

To provide a polymeric ligating clip of the general character described wherein opposed rows of prongs impale a vascular wall or tissue for improved retention and eliminate slippage is another aspect of the present invention.

An additional feature of the present invention is to provide a one piece unitary polymeric ligating clip of the general character described having a pair of legs with an inner face of each leg including rows of transverse ribs separated from one another with each rib including a sharp prong projecting away from the inner face of the leg and toward the longitudinal center line of the opposite leg for impaling vascular tissue when the clip is closed.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown.

DESCRIPTION OF THE INVENTION

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein by way of illustration.

Referring now to the drawings the reference numeral 10 denotes a molded one piece polymeric ligating clip constructed in accordance with the invention. The clip 10 includes a pair of legs 12, 14. The leg 12, hereinafter denoted as the upper leg, includes a distal end 16 and a proximal end 18. The leg 14, hereinafter denoted as the lower leg, includes a distal end 20 and a proximal end 22. The proximal ends 18, 22 are joined by an integral unitary hinge 24.

Figure 1:
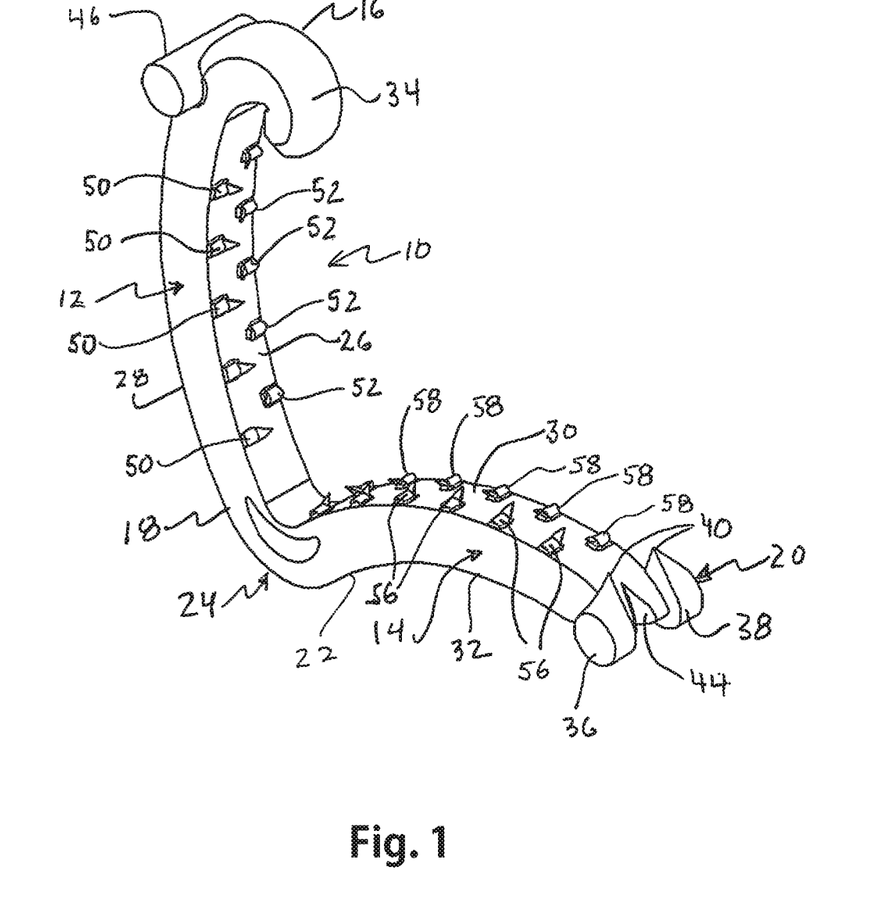
FIG. 1 is an isometric view of a ligating clip constructed in accordance with the invention in an open position and showing a pair of legs, with each leg including two rows of ribs having sharp pointed prongs for engaging vascular or duct walls.
Figure 2:
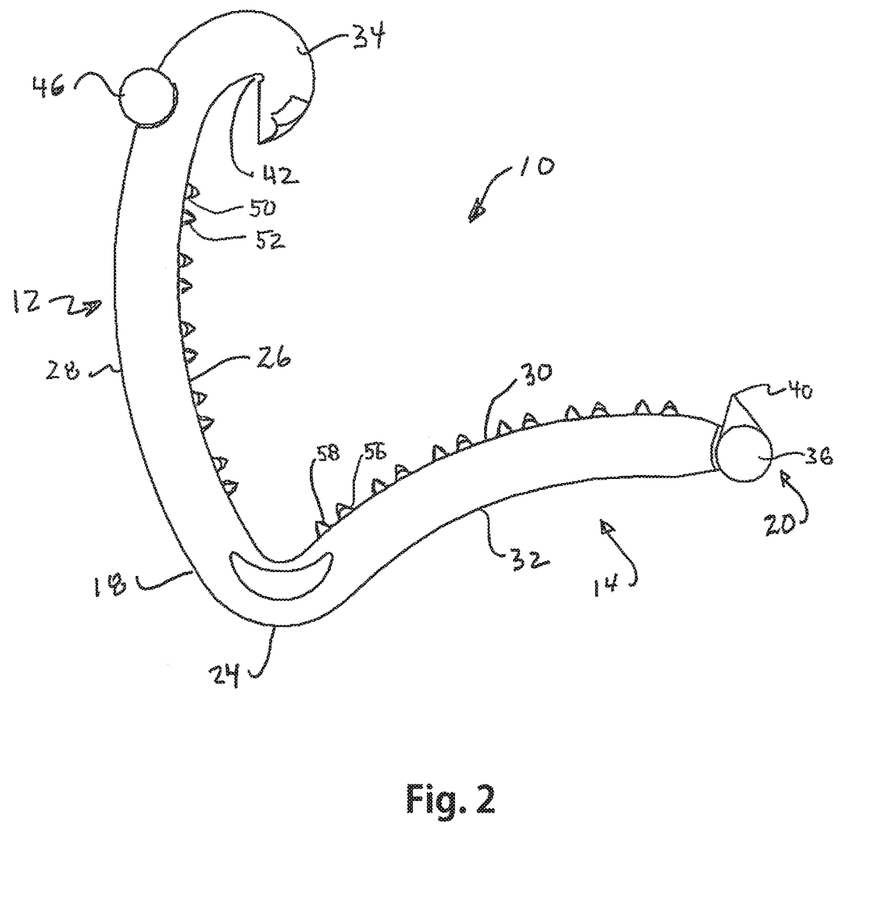
FIG. 2 is a side elevational view of the ligating clip.

As shown in FIGS. 1 and 2, the upper leg 12 has a concave inner vessel clamping face 26 and a convex outer face 28, while the lower leg 14 has a convex inner vessel clamping face 30 and a concave outer face 32.

Figure 11:
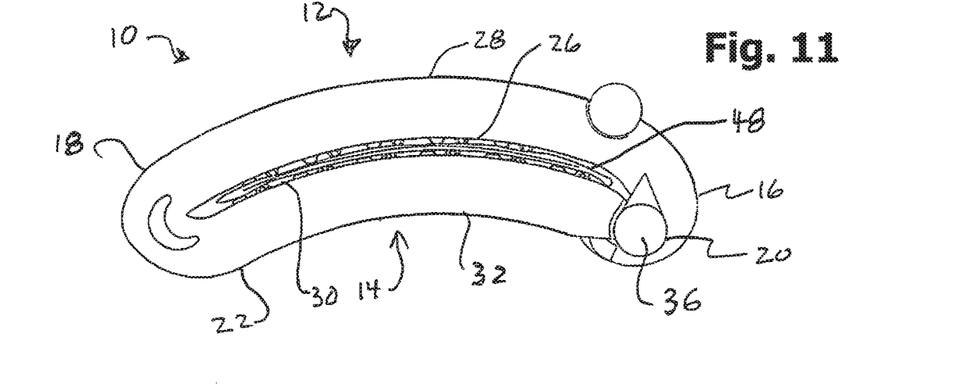
FIG. 11 is a side elevation view of the ligating clip, with the clip closed and latched.

To provide a latch for joining the distal ends 16, 20, the upper leg 12 includes a curved hook 34, at its distal end 16, while the lower leg 14 includes a pair of bosses 36, 38, each having a pointed tip 40, at its distal end 20. The hook 34 has a transverse beveled face and an interned concave inner face which defines a latching recess 42. The latching recess 42 is adapted to pass through a notch 44 formed in the distal end 20 of the lower leg 14 and centered between the bosses 36, 38 the when compressing the clip 10 into a latched or locked position (illustrated in FIG. 11).

In the practice of ligating a vessel as understood by persons skilled in the art, the clip 10 is designed to be compressed into a latched or locked position around a vessel or duct 48 through the use of an appropriate clip applicator instrument, such as described in U.S. Pat. No. 5,100,416, No. 5,062,846 or No. 6,863,675, all of which are incorporated herein by reference. The clip applicator instrument engages a boss 46 adjacent the distal end 16 of the upper leg 12 and the pair of bosses 36, 38 at the distal end 20 of the lower leg 14 to pivot the legs 12, 14 inwardly about the hinge 24. This causes the legs 12, 14 to close around the vessel 48, with the concave inner face 26 of the leg 12 and complementary convex inner face 30 of the leg 14 contacting the outer wall or tissue of the vessel 48, as illustrated in FIGS. 7-10.

Figure 3:
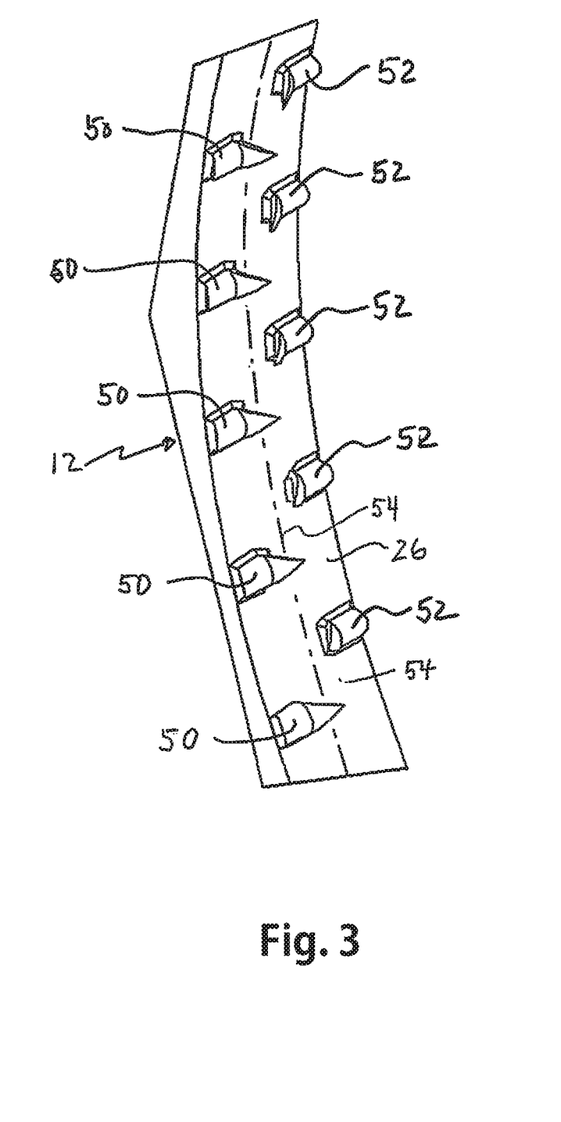
FIG. 3 is an enlarged scale cutaway isometric view of an upper leg, showing the ribs of one row being staggered with respect to the ribs of the other row.
Figure 4:
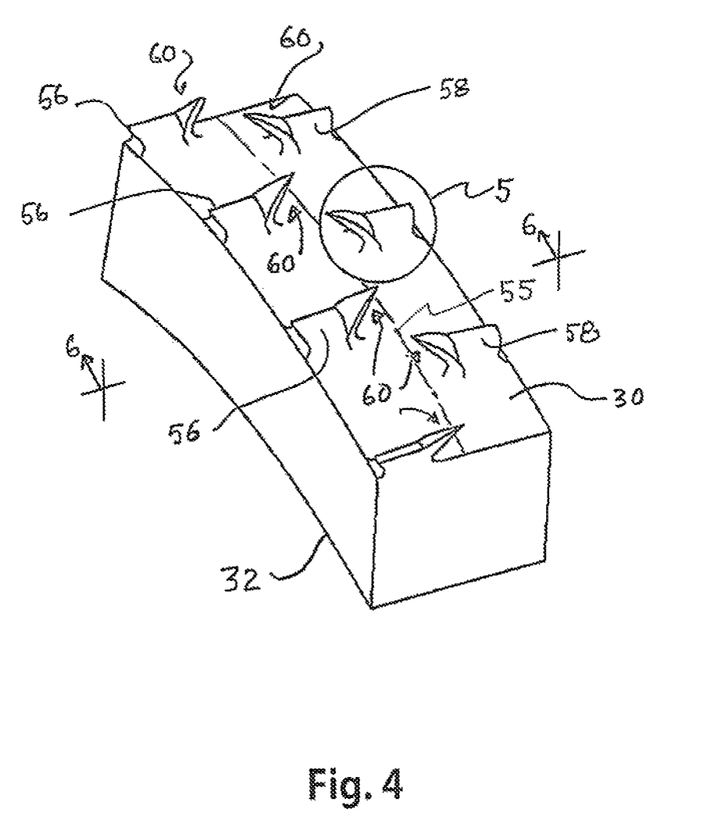
FIG. 4 is an enlarged scale cutaway isometric view of the lower leg.

Pursuant to the invention, the inner face 26 of the upper leg 12 includes two rows of transverse ribs 50, 52, with the rows separated from one another along the longitudinal center line of the inner face of the upper leg 12, (illustrated as a dot and dash line 54 in FIG. 3). The ribs 50 of one row are staggered with respect to the ribs 52 of the other row. Similarly, the inner face 30 of the lower leg 14 includes two rows of transverse ribs 56, 58, with the rows separated from one another along the longitudinal center line 55 of the inner face of the lower leg 14. The ribs 56 of one row are staggered with respect to the ribs 58 of the other row as well as all ribs 50, 52 of the leg 12.

Figure 5:
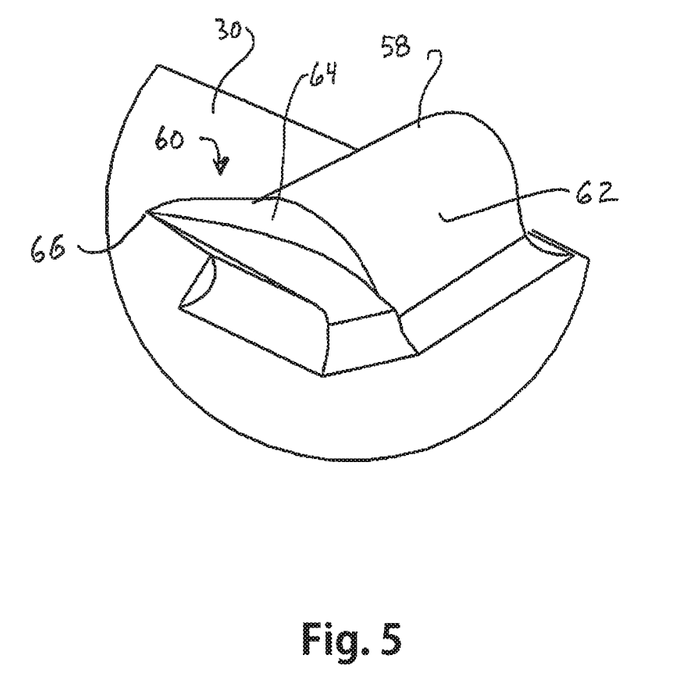
FIG. 5 is an enlarged scale isometric view of a single rib depicted in the circle 5 of FIG. 4.
Figure 6:
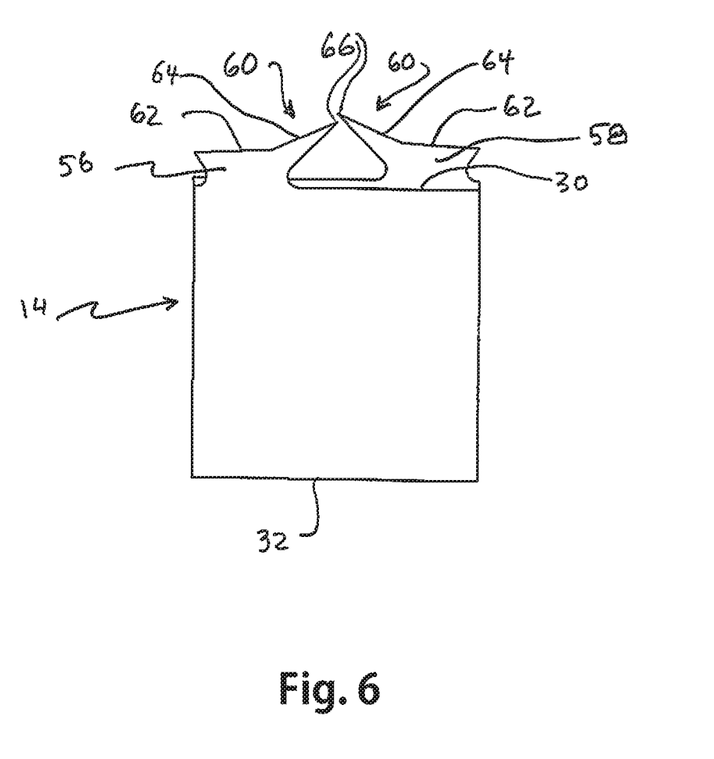
FIG. 6 is an enlarged scale cross sectional view through the lower leg, the same being taken along the plane 6-6 of FIG. 4.
Figure 7:
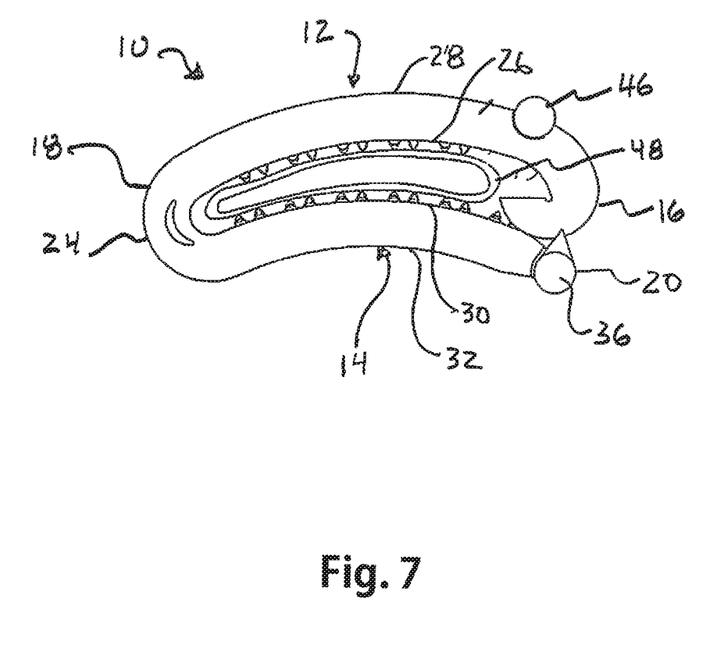
FIG. 7 is a side elevation view of the ligating clip taken as the clip is beginning to clamp a vessel, which is shown in section and with an applicator tool omitted.
Figure 8:
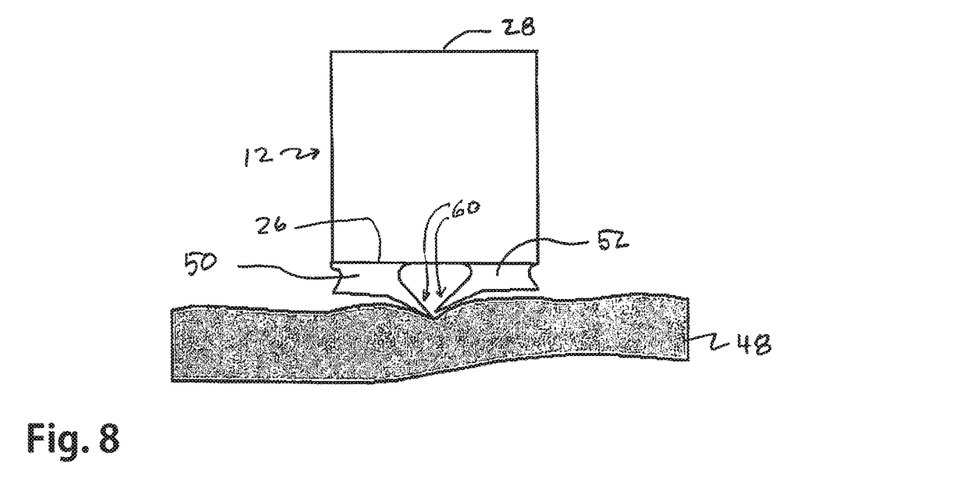
FIG. 8 is an enlarged scale transverse sectional view through the clip and vessel of FIG. 7, taken along broken planes and showing initial engagement between the prongs and the wall of the vessel.
Figure 9:
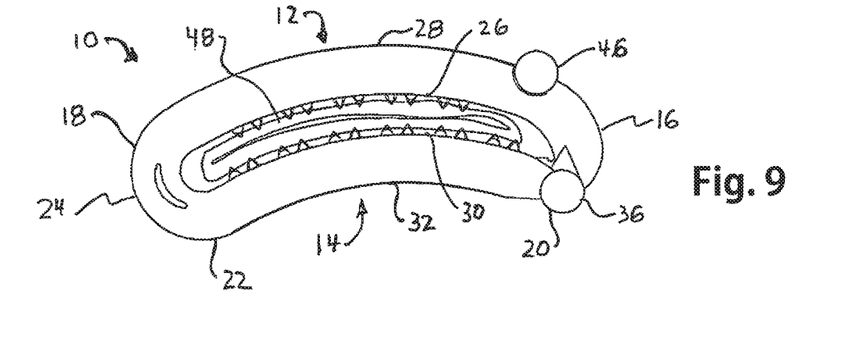
FIG. 9 is a side elevation view of the ligating clip taken as the clip continues to clamp the vessel, but prior to latching the legs.

Each rib 50, 52, 56 and 58 includes a flexible sharp pointed prong 60 which projects away from the inner face of the respective leg and toward the longitudinal center of the inner face of the opposite leg. As best seen in FIG. 5, the rib 58 projects outwardly from the inner face 30 and may include a cylindrically curved base 62, with the sharp pointed prong 60 comprising a sloped bevel tapered projection 64 extending from the base and having a sharp point 66 at its distal end. The ribs 50, 52 and 56 are of identical construction.

Figure 10:
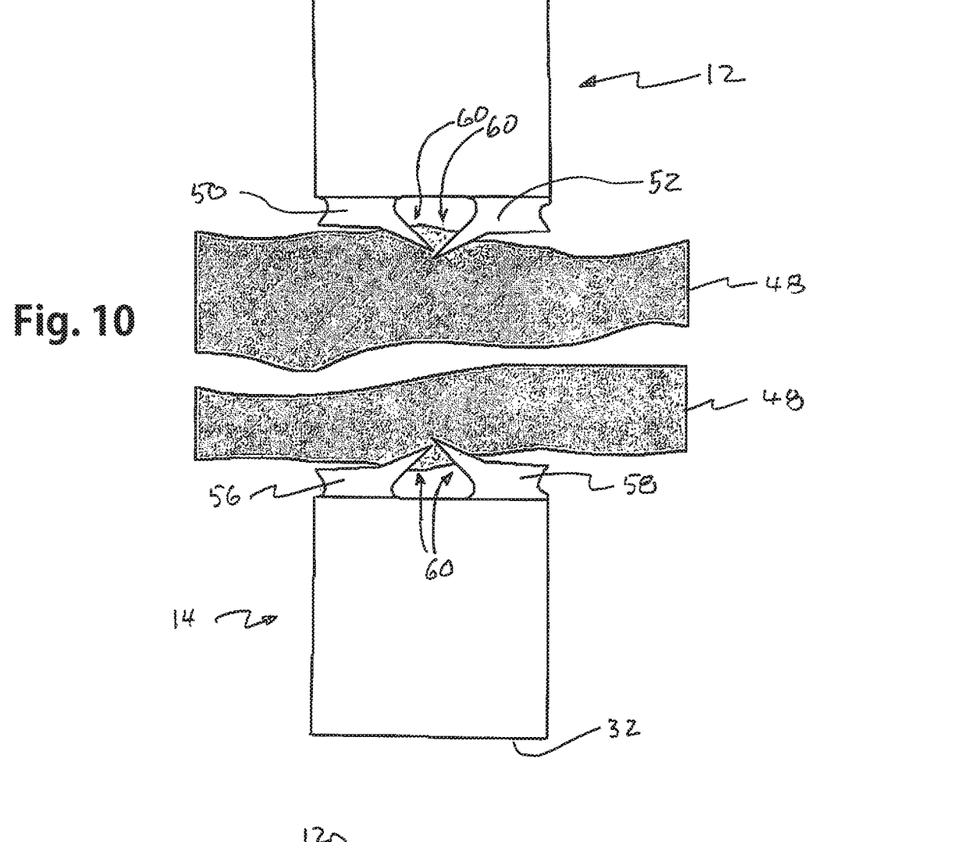
FIG. 10 is an enlarged scale staggered transverse sectional view through the clip and vessel of FIG. 9, taken along a broken plane.
Figure 12:
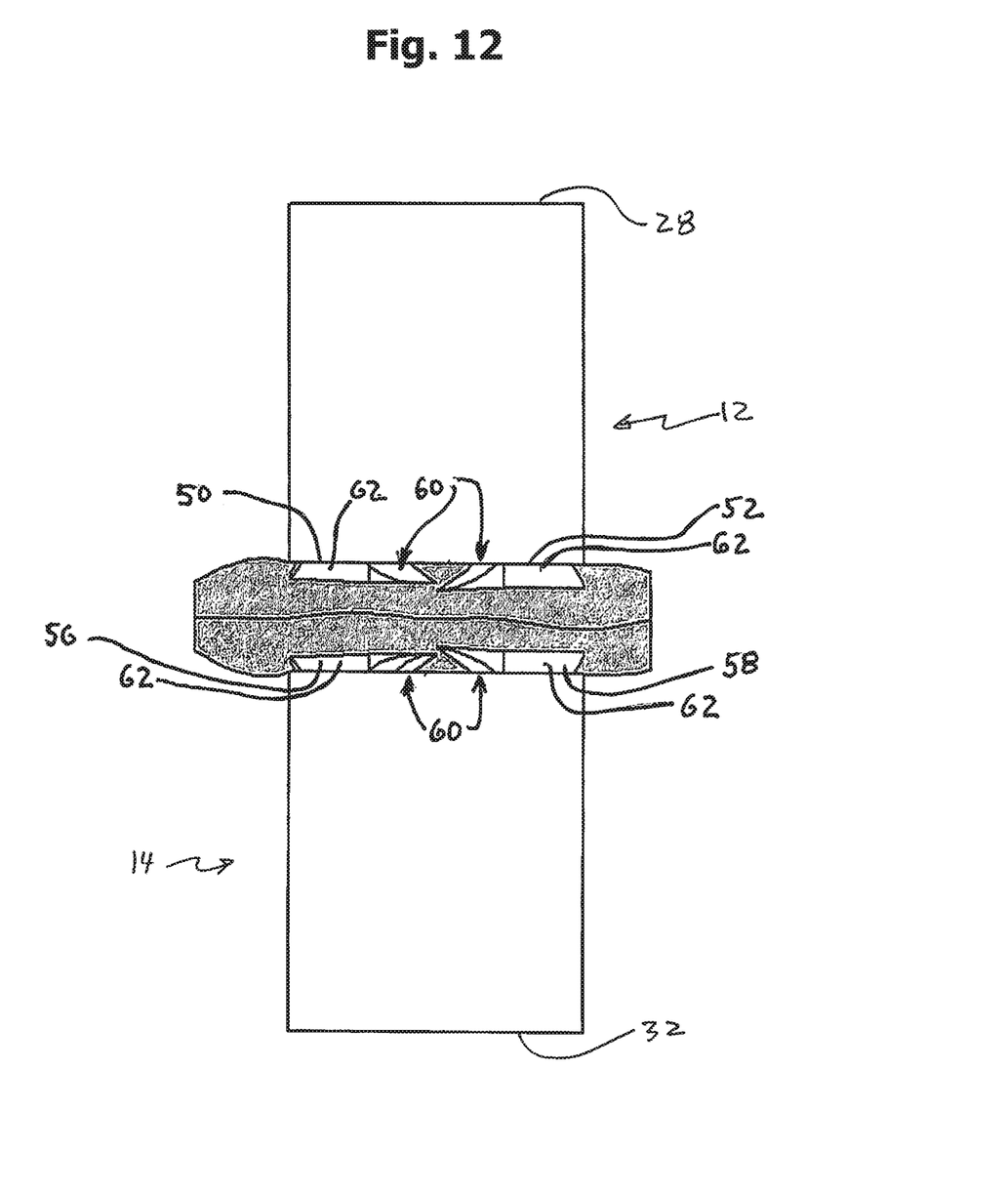
FIG. 12 is an enlarged scale transverse view through the clip and vessel of FIG. 11 taken along broken planes, showing the vessel fully closed with the sharp pointed prongs impaled into to the vessel wall.

As the upper leg 12 and the lower leg 14 close around the vessel or duct 48, the compressive force urges the sharp points 66 of the tapered projections 64 into the vessel wall, as depicted in FIG. 10. Continued closure of the legs 12, 14 urges portions of the vessel wall into the gaps or spaces between the ribs 50, 52, 56 and 58 and flattens the slope of the flexible tapered projections 64 so that the sharp points 66 do not penetrate completely through the vessel wall, as depicted in FIG. 12, thereby minimizing tissue trauma as the vessel is ligated. The clip 10 is thus secured to the vessel 48 with improved retention and reduced slippage, whereby movement of the clip 10 or vessel 48 relative to one another during or after clip closure is prevented.

Thus it will be seen that there is provided a polymeric ligating clip which achieves the various aspects, features and considerations of the present invention and which is well suited to meet the conditions of practical usage.

In the figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element or step, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention as claimed. It is felt therefore that these embodiments should not be limited to the disclosed embodiment but rather should be limited only by the spirit and scope of the appended claims.

Having thus described the invention there is claimed as new and desired to be secured to letters patent:

1. In a ligating clip comprising a first leg and a second leg, each leg having a proximal end and a distal end, the legs being joined at their proximal ends by a hinge, each leg having an inner face and an outer face, the legs being pivotable about the hinge from an open position, wherein the inner faces of the legs may be positioned about a vessel or duct, to a closed position, wherein the distal ends are joined by a latch and the vessel or duct may be compressed between the inner faces of both legs, a first row of evenly spaced ribs projecting from the inner face of the first leg and a second row of evenly spaced ribs projecting from the inner face of the first leg, the rows being spaced from one another about a longitudinally extending center line along the inner face of the first leg, the ribs of the first row being staggered with respect to the ribs of the second row, the improvement comprising at least one rib of the first row including a base extending from the inner face of the first leg, the base having one end facing the longitudinally extending center line of the inner face of the first leg, and a prong having a sharp point projecting beyond the one end of the base and away from the inner face of the first leg, the prong of the first row projecting toward a longitudinally extending center line along the length of the inner face of the second leg, at least one rib of the second row including a base extending from the inner face of the first leg, the base of the at least one rib of the second row having one end facing the longitudinally extending center line of the inner face of the first leg, and a prong having a sharp point projecting beyond the one end of the base of the at least one rib of the second row and away from the inner face of the first leg, the prong of the second row projecting toward the longitudinally extending center line of the inner face of the second leg, whereby the sharp points of the prongs may impale a wall of a vessel or duct and prevent movement of the clip relative to the vessel or duct when the clip is in the closed position while minimizing tissue trauma.

2. The improved ligating clip in accordance with claim 1, the improvement further comprising a third row of evenly spaced ribs, the ribs of said third row projecting from the inner face of the second leg and a fourth row of evenly spaced ribs, the ribs of said fourth row projecting from the inner face of the second leg, the third and fourth rows being spaced from one another along the longitudinally extending center line of the inner face of the second leg, the ribs of the third row being staggered with respect to the ribs of the fourth row and with respect to the ribs of the first and second rows, at least one rib of the third row having a base extending from the inner face of the second leg, the base having one end facing the longitudinally extending center line of the inner face of the second leg, and including a prong having a sharp point projecting beyond the one end of the base of the least one rib of the third row and away from the inner face of the second leg, the prong projecting toward the longitudinally extending center line of the inner face of the first leg, at least one rib of the fourth row having a base extending from the inner face of the second leg, the base having one end facing the longitudinally extending center line of the inner face of the second leg and a prong having a sharp point projecting beyond the one end of the base of the at least one rib of the fourth row and away from the inner face of the second leg and projecting toward the longitudinally extending center line of inner face of the first leg, whereby the sharp points of the prongs of both legs may impale the wall of the vessel or duct and prevent movement of the clip relative to the vessel or duct when the clip is in the closed position.

3. The improved ligating clip in accordance with claim 2, wherein all of the ribs include a base and a prong having a sharp point projecting toward the longitudinally extending center line of the inner face of the opposite leg.

4. The improved ligating clip in accordance with claim 3, wherein, the prongs comprise a tapered projection extending beyond the one end of each base, the sharp point being at the end of the tapered projection.

5. The improved ligating clip in accordance with claim 1, wherein all of the ribs include a base and a prong comprising a tapered projection extending beyond the one end of the base, the sharp point being at the end of the tapered projection.

6. A clip for ligating a vessel or duct, the clip comprising first and second legs having respective proximal and distal end portions, the proximal end portions being joined by a hinge, the first and second legs having respective first and second inner faces adapted for positioning about a vessel or duct and which may engage the vessel or duct when said first and second legs are moved about said hinge from an open position to a closed position, wherein the distal end portions are secured together by a latch, said first leg having a first row of evenly spaced ribs, each rib having a base and a tapered prong extending beyond each base toward a longitudinally extending center line of the second inner face, the tapered prong of the first row having a sharp point at its distal end and a second row of evenly spaced ribs, each rib of the second row having a base and a tapered prong extending beyond each base toward the longitudinally extending center line of the second inner face, the tapered prong of the second row having a sharp point at its distal end, whereby the tapered prongs will impale a wall of the vessel or duct and prevent movement of the clip relative to the vessel or duct when the clip is in the closed position.

7. The clip for ligating a vessel or duct in accordance with claim 6 wherein the ribs are staggered with respect to one another.

8. The clip for ligating a vessel or duct in accordance with claim 6 wherein the second leg includes a third row of evenly spaced ribs, each rib of the third row having a base and a tapered prong extending beyond each base toward a longitudinally extending center line of the first inner face, the tapered prong of the third row having a sharp point at its distal end, the second leg further including a fourth row of evenly spaced ribs, each rib of the fourth row having a base and a tapered prong extending beyond each base toward the longitudinally extending center line of the first inner face, the tapered prong of the fourth row having a sharp point at its distal end whereby the prongs of both legs may impale the wall of the vessel or duct and prevent movement of the clip relative to the vessel or duct when the clip is in the closed position.

9. The clip for ligating a vessel or duct in accordance with claim 8 further including a boss adjacent the distal end of the first leg and a pair of spaced bosses at the distal end of the second leg, the distal ends of the first and second legs comprising mating latch components and the bosses being engaged by jaws of an applicator tool to move the legs about the hinge from an open position to a dosed position.

10. A method of ligating a vessel or duct with a clip of claim 9 and an applicator tool, the method comprising the steps of:
 a) grasping the dip by the distal end portions with the applicator tool;
 b) employing the applicator tool to position the inner faces of the legs across the vessel or duct to be ligated;
 c) impaling the sharp pointed prongs into the wall of the vessel or duct by employing the applicator tool to apply compressive force urging the distal end portions together;
 d) terminating step c) when the latch is engaged; and
 e) removing the applicator tool.

11. The method of ligating a vessel or duct in accordance with claim 10 wherein the applicator tool includes a pair of jaws and step a) includes grasping the boss adjacent the distal end portion of the first leg and the bosses at the distal end portion of the second leg with the jaws of the applicator tool.

12. In a ligating clip comprising a first leg and a second leg, each leg having a proximal end and a distal end, the legs being joined at their proximal ends by a hinge, each leg having an inner face and an outer face, the legs being pivotable about the hinge from an open position, wherein the inner faces of the legs may be positioned about a vessel or duct, to a closed position, wherein the distal ends are joined by a latch and the vessel or duct is compressed between the inner faces of both legs, the improvement comprising first and second rows of evenly spaced ribs, the rows being spaced from one another along a longitudinally extending center line of the inner face of the first leg, each rib including a prong, the prongs projecting outwardly from the inner face of the first leg, the prongs being inclined toward the longitudinally extending center line of the inner face of the second leg, whereby the prongs may impale a wall of the vessel or duct and prevent relative movement between the clip and the vessel or duct while minimizing tissue trauma when the clip is in the closed position.

13. The improved ligating clip in accordance with claim 12, the improvement further comprising third and fourth rows of evenly spaced ribs on the inner face of the second leg, each rib including a prong, the rows being spaced from one another along a longitudinally extending center line of the inner face of the second leg, the ribs of the third row being staggered with respect to the ribs of the fourth row and with respect to the ribs of the first leg, each rib of the third and fourth rows including a prong projecting outwardly from the inner face of the second leg, the prongs being inclined toward the longitudinally extending center line of the inner face of the first leg, whereby the prongs of both legs may impale the wall of the vessel or duct and prevent relative movement between the clip and the vessel or duct when the clip is in the closed position.

14. The improved ligating clip in accordance with claim 13 wherein each prong is tapered and includes a sharp point, the sharp point being at the end of the prong.

15. The improved ligating clip in accordance with claim 13, wherein the ligating clip is polymeric and formed of one piece molded construction.

16. The improved ligating clip in accordance with claim 15, wherein the inner face of the first leg is concavely curved and the inner face of the second leg is convexly curved.

17. A method of ligating a vessel or duct with the improved ligating dip of claim 13, the method comprising the steps of:
 a) providing the improved ligating clip in the open position,
 b) grasping the improved ligating clip at or adjacent the distal end of each leg;
 c) positioning the inner faces of the legs across the vessel or duct to be ligated;
 d) impaling the sharp pointed prongs into the wall of the vessel or duct by applying compressive force urging the distal ends together; and
 e) terminating step d) when the latch is engaged.

18. The improved ligating clip in accordance with claim 13 wherein the ribs of the third row are staggered with respect to the ribs of the fourth row and with respect to the ribs of the first leg.

19. The improved ligating clip in accordance with claim 12 wherein each prong is tapered and includes a sharp point, the sharp point being at the end of the prong.

20. The improved ligating clip in accordance with claim 12 wherein the ribs of the first row are staggered with respect to the ribs of the second row.

* * * * *